(12) United States Patent
Hsieh et al.

(10) Patent No.: US 9,303,049 B2
(45) Date of Patent: Apr. 5, 2016

(54) NANODOT AND METHOD FOR MANUFACTURING THE SAME

(71) Applicant: National Sun Yat-sen University, Kaohsiung (TW)

(72) Inventors: Shu-Chen Hsieh, Kaohsiung (TW); Pei-Ying Lin, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 0 days.

(21) Appl. No.: 14/293,051

(22) Filed: Jun. 2, 2014

(65) Prior Publication Data

US 2015/0073167 A1 Mar. 12, 2015

(30) Foreign Application Priority Data

Sep. 6, 2013 (TW) .............................. 102132114 U

(51) Int. Cl.
*G01N 33/552* (2006.01)
*C07F 7/18* (2006.01)
*A61K 49/00* (2006.01)
*B82Y 15/00* (2011.01)

(52) U.S. Cl.
CPC ........... *C07F 7/1836* (2013.01); *A61K 49/0067* (2013.01); *B82Y 15/00* (2013.01); *Y10S 977/774* (2013.01); *Y10S 977/897* (2013.01)

(58) Field of Classification Search
USPC .......................... 436/525, 527, 528, 532, 535
See application file for complete search history.

(56) References Cited

U.S. PATENT DOCUMENTS 4,628,037 A * 12/1986 Chagnon et al. .............. 436/526

* cited by examiner

*Primary Examiner* — Sudhakar Katakam
*Assistant Examiner* — Pancham Bakshi
(74) *Attorney, Agent, or Firm* — Birch, Stewart, Kolasch & Birch, LLP

(57) ABSTRACT

The present disclosure provides a method for manufacturing a nanodot, including: providing a hydrolysable silane, wherein the hydrolysable silane has one or more hydrolysable groups and one or more substituted or non-substituted hydrocarbon groups; and performing a one-step heat treatment to hydrolyze and condensate the hydrolysable silane to form a nanodot. The nanodot includes: a core, the core is selected from the group consisting of a semiconductor core or a metal core; and a self-assembled monolayer (SAM) including the substituted or non-substituted hydrocarbon groups, wherein the self-assembled monolayer is connected to the core by covalent bonds.

9 Claims, 14 Drawing Sheets
(5 of 14 Drawing Sheet(s) Filed in Color)

NANODOT AND METHOD FOR MANUFACTURING THE SAME

CROSS REFERENCE TO RELATED APPLICATIONS

This application claims priority of Taiwan Patent Application No. 102132114, filed on Sep. 6, 2013, the entirety of which is incorporated by reference herein.

BACKGROUND

1. Technical Field

The disclosure relates to a nanodot and a method for manufacturing the same, and in particular to a nanodot having a self-assembled monolayer and a method for manufacturing the same.

2. Description of the Related Art

Nanoparticles have a surface effect, a quantum size effect and a quantum tunneling effect. Therefore they have unique electrical, chemical and physical properties and may be applied in many aspects, such as in the optoelectronics field or the biological field.

For example, the carbon dot is a conventional nanodot. It exhibits multiphoton fluorescence and thus is suitable for application in an optoelectronic device and in intravital imaging such as the detection of biomolecules in vivo and the real-time monitoring of enzyme activities. However, the preparation process of the carbon dot is complicated and needs harsh conditions. Besides, it is difficult to control the resulting carbon dot size. Therefore, a simple and size-controllable process for preparing a nanodot is needed.

SUMMARY

The present disclosure provides a method for manufacturing a nanodot, including: providing a hydrolysable silane, wherein the hydrolysable silane has one or more hydrolysable groups and one or more substituted or non-substituted hydrocarbon groups; and performing a one-step heat treatment to hydrolyze and condensate the hydrolysable silane to form a nanodot, wherein the nanodot includes: a core, the core is selected from the group consisting of a semiconductor core or a metal core; and a self-assembled monolayer (SAM) including the substituted or non-substituted hydrocarbon groups, wherein the self-assembled monolayer is connected to the core by covalent bonds.

The present disclosure also provides a nanodot, including: a core, the core is selected from the group consisting of a semiconductor core or a metal core; and a self-assembled monolayer (SAM) including substituted or non-substituted hydrocarbon groups, wherein the self-assembled monolayer is connected to the core by covalent bonds.

A detailed description is given in the following embodiments with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The disclosure may be more fully understood by reading the subsequent detailed description and examples with references made to the accompanying drawings, wherein.

DETAILED DESCRIPTION

Figure 1:
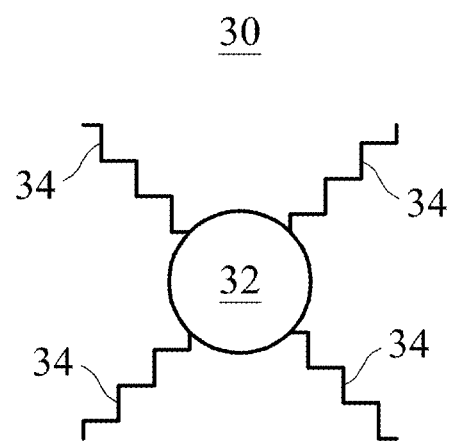
FIG. 1 is a schematic view of a nanodot in accordance with some embodiments of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

Unless defined otherwise, all technical and scientific terms used herein have the same meaning as commonly understood to one of ordinary skill in the art to which this disclosure belongs. It should be appreciated that, in each case, the term, which is defined in a commonly used dictionary, should be interpreted as having a meaning that conforms to the relative skills and the background or the context of the present disclosure, and should not be interpreted in an idealized or overly formal manner unless defined otherwise.

The terms "about" and "substantially" typically mean +/−20% of the stated value, more typically +/−10% of the stated value and even more typically +/−5% of the stated value. The stated value of the present disclosure is an approximate value. When there is no specific description, the stated value includes the meaning of "about" or "substantially".

The method for manufacturing the nanodot provided in the present disclosure utilizes a one-step heat treatment to hydrolyze and condensate the hydrolysable silane to form a nanodot. In this method, a hydrolysable silane is first provided. The hydrolysable silane has one or more hydrolysable groups and one or more substituted or non-substituted hydrocarbon groups. In one embodiment, this hydrolysable silane has a general formula (1):

$$SiR^1{}_xR^2{}_{(4-x)} \quad (I)$$

wherein x is 2 or 3. $R^1$ is the hydrolysable group and includes a halogen or $C_1$ to $C_5$ alkoxy group. $R^2$ is the substituted or non-substituted hydrocarbon groups and the substituent group is an alkyl group, a haloalkyl group, a thiol group, an amino group or an aryl group. The substituted or non-substituted hydrocarbon groups may include 3-22 carbon atoms. For example, the substituted or non-substituted hydrocarbon group of an n-octadecyltriethoxysilane nanodot has 18 carbon atoms. The molecular weight of the hydrolysable silane may range from about 90 to 135. For example, the molecular weight of an n-octadecyltriethoxysilane nanodot range from about 100 to 300.

In one embodiment, the hydrolysable silane may be n-hexyltriethoxysilane, n-dodecyltriethoxysilane, n-octadecyltriethoxysilane, 3-aminopropyltriethoxysilane, 4-aminobutyltriethoxysilane, 5-aminopentyltriethoxysilane, 6-aminohexyltriethoxysilane, 3-aminopropyltrichlorosilane, 4-aminobutyltrichlorosilane, 5-aminopentyltrichlorosilane, 6-aminohexyltrichlorosilane, 3-mercaptopropyltriethoxysilane, 4-mercaptobutyltriethoxysilane, 5-mercaptopentyltriethoxysilane, 6-mercaptohexyltriethoxysilane, 3-mercaptopropyltrichlorosilane, 4-mercaptobutyltrichlorosilane, 5-mercaptopentyltrichlorosilane, 6-mercaptohexyltrichlorosilane, 3-phenylpropyltriethoxysilane, 4-phenylbutyltriethoxysilane, 5-phenylpentyltriethoxysilane, 6-phenylhexyltriethoxysilane, 3-phenylpropyltrichlorosilane, 4-phenylbutyltrichlorosilane, 5-phenylpentyltrichlorosilane, 6-phenylhexyltrichlorosilane, 6,6,6-trifluoro n-hexyltriethoxysilane, 12,12,12-trifluoro n-dodecyltriethoxysilane, 18,18,18-trifluoro n-octadecyltriethoxysilane, 6,6,6-trichloro n-hexyltriethoxysilane, 12,12,12-trichloro n-dodecyltriethoxysi lane, 18,18,18-trichloro n-octadecyltriethoxysilane, 6,6,6-tribromo n-hexyltriethoxysilane, 12,12,12-tribromo n-dodecyltriethoxysilane, 18,18,18-tribromo n-octadecyltriethoxysilane, 6,6,6-trifluoro n-hexyltrichlorosilane, 12,12,12-trifluoro n-dodecyltrichlorosilane, 18,18,18-trifluoro n-octadecyltrichlorosilane, 6,6,6-trichloro n-hexyltrichlorosilane, 12,12,12-trichloro n-dodecyltrichlorosilane, 18,18,18-trichloro n-octadecyltrichlorosilane, 6,6,6-tribromo n-hexyltrichlorosilane, 12,12,12-tribromo n-dodecyltrichlorosilane, 18,18,18-tribromo n-octadecyltrichlorosilane, (3-mercaptopropyl)trimethoxysilane, n-butyltrichlorotin, phenylmethyldimethoxysilane, titanium(IV) ethoxide or any other suitable silanes.

Then a one-step heat treatment is performed to hydrolyze and condensate the hydrolysable silane to form a nanodot. In this one-step heat treatment, the hydrolysable silane is hydrolyzed. The hydrolysable group of the hydrolysable silane leaves and a silanol group is formed. Then the silanol group may be condensated with other hydrolysable silane to form a siloxane linkage. In one embodiment, the one-step heat treatment is performed at a temperature ranging from about 120° C. to 220° C. for about 30 minutes to 9 hours. For example, n-octadecyltriethoxysilane nanodot may be heated under 200° C. for 3 hours. In addition, the one-step heat treatment may be performed with the hydrolysable silane being stirred. For example, the heating may be performed with the hydrolysable silane being stirred at about 1100 rpm. It should be noted that the conventional preparation process of a nanodot (such as a carbon dot) is complicated and needs harsh conditions. Besides, it is difficult to control the size of the resulting nano material prepared by the conventional process.

The present disclosure utilizes only one-step heat treatment to prepare the nanodot. In addition, the particle size of the nanodot could be controlled by selecting the length of the substituted or non-substituted hydrocarbon group. Furthermore, the nanodot prepared by the method of the present disclosure has a uniform particle size distribution. The standard deviation of the particle size distribution may range from about 2 nm to 7 nm. For example, the standard deviation of the particle size distribution of an n-octadecyltriethoxysilane nanodot is 4.52±1.09 nm.

In one embodiment, referring to FIG. 1A, the nanodot includes a core 32 and a self-assembled monolayer 34. The core 32 may be a semiconductor core or a metal core. In one embodiment, the semiconductor core may be a silicon oxide core 32. The silicon oxide core 32 may include 4-20 silicon atoms. For example, the silicon oxide core of an n-octadecyltriethoxysilane nanodot may include 4-6 silicon atoms. The silicon atoms are connected to each other by a siloxane linkage. The self-assembled monolayer 34 includes substituted or non-substituted hydrocarbon groups, and the substituent group may include an alkyl group, a haloalkyl group, a thiol group, an amino group, an aryl group or any other suitable groups. The self-assembled monolayer 34 is connected to the silicon oxide core 32 by covalent bonds. The substituted or non-substituted hydrocarbon groups may include 12-88 carbon atoms. For example, the substituted or non-substituted hydrocarbon groups of an n-octadecyltriethoxysilane nanodot may include 72 carbon atoms. The molecular weight of the nanodot 30 may range from 800 to 2400. For example, the molecular weight of an n-octadecyltriethoxysilane nanodot may range from 1600 to 1680. The particle size of the nanodot 30 ranges from 2 nm to 7 nm. For example, the particle size of an n-octadecyltriethoxysilane nanodot may be 4.52±1.09 nm. It should be noted that since the nanodot 30 of the present disclosure has a self-assembled monolayer 34, aggregation between the nanodots 30 can be prevented. In addition, since the self-assembled monolayer 34 may serve as a protection layer to prevent the nanodot 30 from reacting with other hydrolysable silanes, the preparation method of the present disclosure has a reaction self-termination effect.

Figure 2:
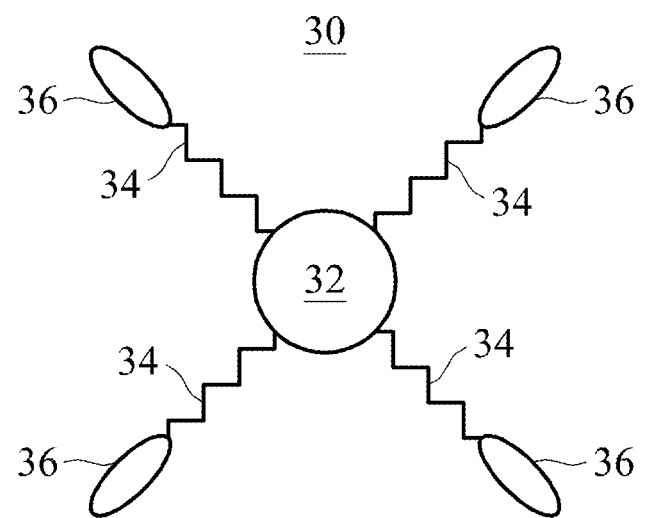
FIG. 2 is a schematic view of a nanodot modified by a biomolecule in accordance with some embodiments of the present disclosure.

In one embodiment, the substituent group of self-assembled monolayer 34 may be a terminal amino group that may form an amide bond. In this embodiment, referring to FIG. 2, a biomolecule 36 may be added after the one-step heat treatment to modify the self-assembled monolayer 34. The biomolecule 36 may be a specific recognition molecule. The specific recognition molecule may include, but is not limited to, antibody, protein, peptide, enzyme, saccharide (carbohydrate), glycoprotein, nucleic acid or lipid. Those skilled in the art may choose the specific recognition molecule according to the practical requirements to obtain various labeled nanodots with enhanced targeting efficiency. For example, Folic acid may be used to specifically recognize the folate receptor of breast cancer. Avidin may be used to specifically recognize the biotin of SK-Hep-1 cell. Galactose may be used to specifically recognize the asialoglycoprotein receptor (ASGP-R) of HepG2 cell and HeLa cell. In this embodiment, Folic acid, avidin or galactose may be coupled to the self-assembled monolayer 34 by forming an amide bond (—CONH—) with the terminal amino group of the self-assembled monolayer 34. The particle size of the nanodot 30 after being modified by the biomolecule 36 may range from 3 nm to 15 nm. For example, the particle size of 3-aminopropyltriethoxysilane nanodot after being modified by galactose may range from 3 nm to 5 nm.

In one embodiment, the quantum yield of the nanodot ranges from about 3% to 46%, and the quantum yield may be tuned by tuning the particle size of the nanodot. The nanodot has an emission wavelength ranging from about 300 nm to 600 nm. For example, the nanodot may exhibit multiphoton fluorescence with significant red, green and blue lights emitted when excited by an excitation light with different wavelengths. In addition, there are many factors that may affect the emission property of the nanodot, such as carbon defect, non-bridging oxygen or other species within the silicon matrix. It was discovered that the peak maximum position of the photoluminescence spectrum of the nanodot is related to the particle size. The peak maximum position may be tuned by altering the particle size of the nanodot. Since the nanodot of the present disclosure has good quantum yield and multiphoton fluorescence property, it is suitable for application in the fields of bioimaging and optoelectronic elements.

The test of survival stress of the nanodot on a living creature shows that it has good biocompatibility. For example, a zebrafish was fed a nanodot. The survival rate of the zebrafish fed with the nanodot was observed in comparison with the survival rate of zebrafish not fed with the nanodot. It was showed that the nanodot has no significant effect on the survival rate of the zebrafish. For example, in one experiment, the difference between the 7-day post survival rates of the zebrafish fed with the nanodot and the zebrafish not fed with the nanodot was merely 10% (the survival rate of the zebrafish fed with the nanodot=80±10%, the survival rate of the zebrafish not fed with the nanodot=90±10%). Therefore, due to the good biocompatibility of the nanodot, it can be applied in bio-related research and application. For example, in one embodiment, the hydrocarbon group of the nanodot has a terminal amino group modified with a protein molecule or a saccharide molecule. Since the protein molecule and the saccharide molecule can specifically interact with other biomolecules, the nanodot may serve as a bioprobe. In other embodiments, the nanodot may be applied in bioimaging, disease detection, cancer diagnosis and protein and drug tracking. In still another embodiment, the nanodot may be applied in an optoelectronic element.

In summary, the method for manufacturing the nanodot of the present disclosure needs only one-step heat treatment to prepare the nanodot. This method can prevent the aggregation between the nanodots and has a reaction self-termination effect. In addition, the nanodot prepared using this method has a uniform particle size distribution, and the particle size is controllable. Furthermore, the nanodot of the present disclosure has high quantum yield, multiphoton fluorescence property and good biocompatibility. Therefore it is suitable for application in the bio-related field or the optoelectronic field.

COMPARATIVE EXAMPLE

Comparative Example 1

Figure 10:
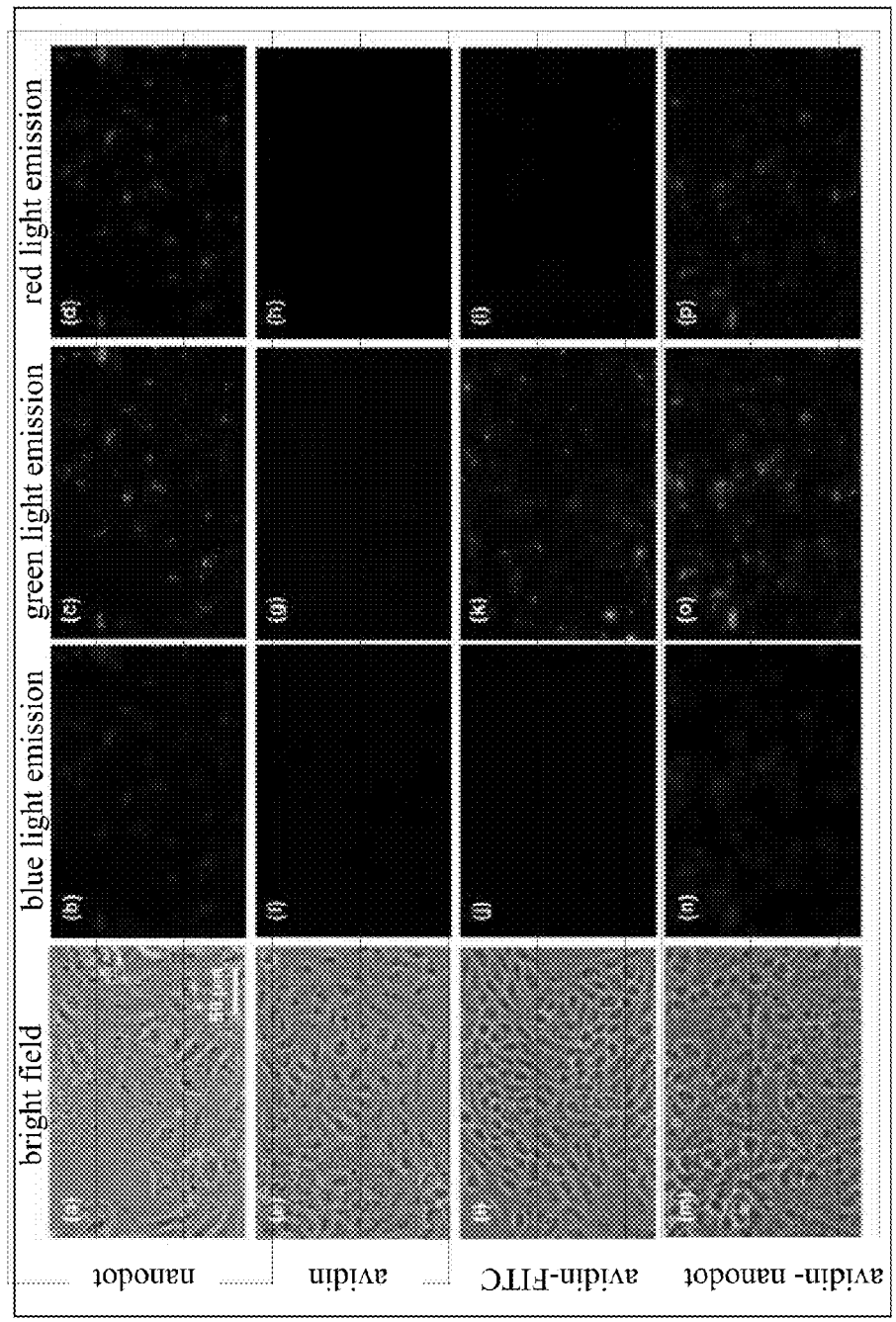
FIG. 10 is a fluorescence microscopy with nanodot, avidin, avidin-FITC or avidin-nanodot under a bright field or under other different excitation light sources.

SK-Hep-1 cell was incubated under 37° C. for 12 hours (overnight). Then avidin (purchased from Sigma) was added into the SK-Hep-1 cell to form a cell culture. After 48 hours, the cell culture was rinsed with PBS (phosphate buffered saline). Then the cell was fixed by paraformaldehyde. The cell culture was perfused by 2% Triton X-100 (also referred to as polyethylene glycol p-(1,1,3,3-tetramethylbutyl)-phenyl ether) and was observed by an inverted fluorescence microscope (Leica, DMIL, Germany). FIGS. 10($e$)-($h$) show the images under a bright field or under other different excitation light sources.

Comparative Example 2

SK-Hep-1 cell was incubated under 37° C. for 12 hours (overnight). Then avidin-FITC (purchased from Sigma) was added into the SK-Hep-1 cell to form a cell culture. The FITC ((Flourescein Isothiocyanate) was a conventional organic fluorescent dye and was widely applied in bioimaging. After 48 hours, the cell culture was rinsed with PBS (phosphate buffered saline). Then the cell was fixed by paraformaldehyde. The cell culture was perfused by 2% Triton X-100 (also referred to as polyethylene glycol p-(1,1,3,3-tetramethylbutyl)-phenyl ether) and was observed by an inverted fluorescence microscope (Leica. DMIL, Germany). FIGS. 10($i$)-($l$) show the images under a bright field or under other different excitation light sources.

EXAMPLE

Figure 3:
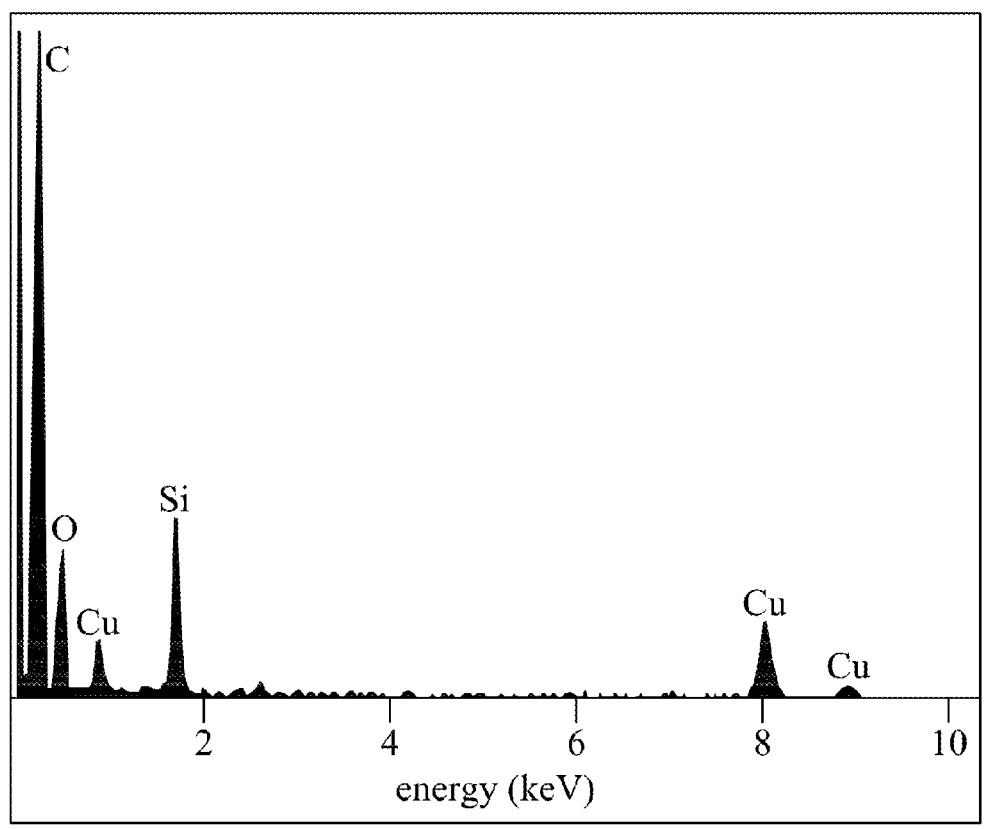
FIG. 3 is an energy dispersive X-ray spectrometry of a nanodot in accordance with some embodiments of the present disclosure.
Figure 4:
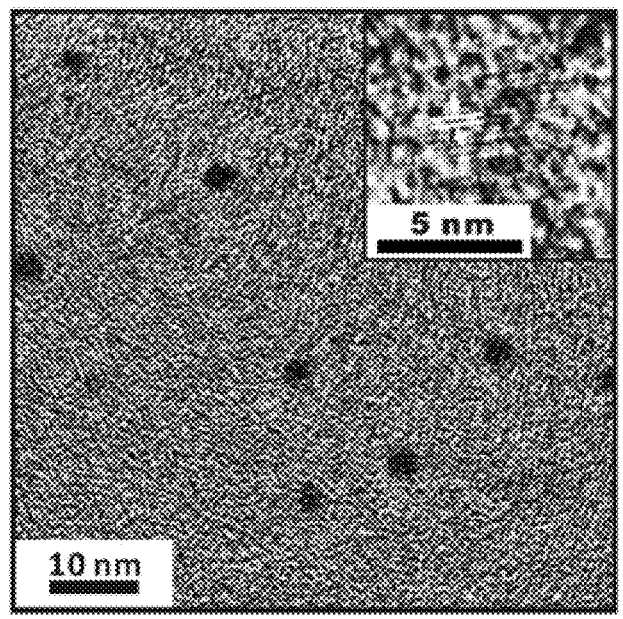
FIG. 4 is a transmission electron microscopy of a nanodot in accordance with some embodiments of the present disclosure.

Example 1 n-Hexyltriethoxysilane (purity>95%) was purchased from Gelest (USA) and used without further purification. n-Hexyltriethoxysilane was heated at to 200° C. and stirred (1100 rpm) at a constant temperature of 200 for 3 hours to prepare n-hexyltriethoxysilane nanodot solution. The prepared n-hexyltriethoxysilane nanodot was analyzed by energy dispersive X-ray spectrometry EDS, as shown in FIG. 3. This figure indicates the presence of Si, O, and C as the primary chemical components. In addition, the n-hexyltriethoxysilane nanodot was analyzed by transmission electron microscopy (TEM), as shown in FIG. 4. This figure indicates no aggregation occurred between the prepared n-hexyltriethoxysilane nanodot. FIG. 4 also shows that the nanodot had a silicon oxide core (dark region) and a self-assembled monolayer (bright region).

Example 2 n-Docccyltriethoxysilane (purity>95%) was purchased from Gelest (USA) and used without further purification. n-Docecyltriethoxysilane was heated at to 200° C. and stirred (1100 rpm) at a constant temperature of 200° C. for 3 hours to prepare n-docecyltriethoxysilane nanodot solution.

Example 3 n-Octadecyltriethoxysilane (purity>95%) was purchased from Gelest (USA) and used without further purification. n-Octadecyltriethoxysilane was heated at to 200° C. and stirred (1100 rpm) at a constant temperature of 200° C. for 3 hours to prepare n-octadecyltriethoxysilane nanodot solution.

[Raman Spectrum Analysis]

Figure 5:
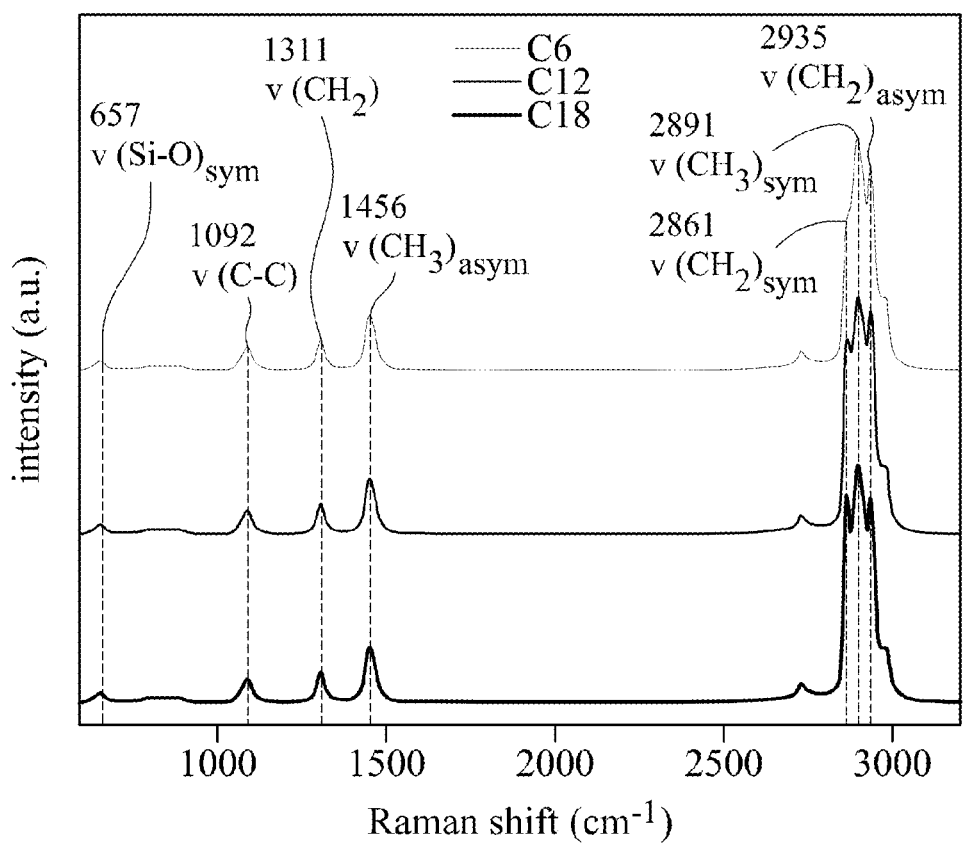
FIG. 5 is a Raman spectra of a nanodot in accordance with some embodiments of the present disclosure.

The nanodots prepared in examples 1-3 were analyzed by Raman spectrum, as shown in FIG. 5. The peaks at 657 $cm^{-1}$, 1092 $cm^{-1}$, 2861 $cm^{-1}$, 2935 $cm^{-1}$ respectively corresponded to Si—O stretch, C—C stretch, the symmetric and asymmetric —$CH_2$— stretching. This analysis of the bonding type indicated that the nanodot of the present disclosure had a silicon oxide core and a self-assembled monolayer.

[Atomic Force Microscopy Analysis]

Figure 6A:
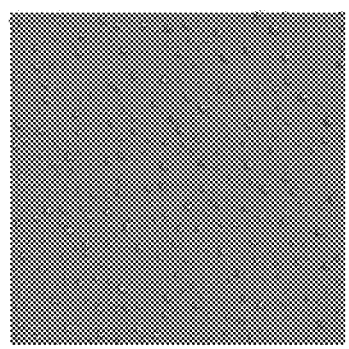
FIGS. 6A-6C are atomic force microscopies of a nanodot in accordance with some embodiments of the present disclosure.
Figure 6B:
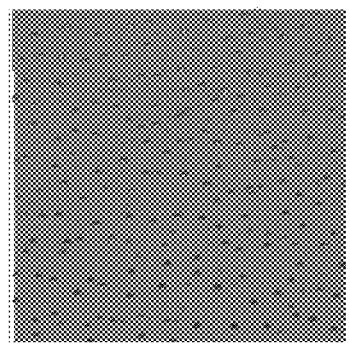
Figure 6C:
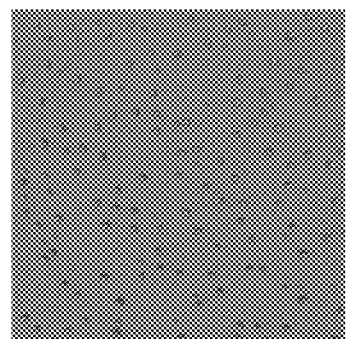
Figure 7A:
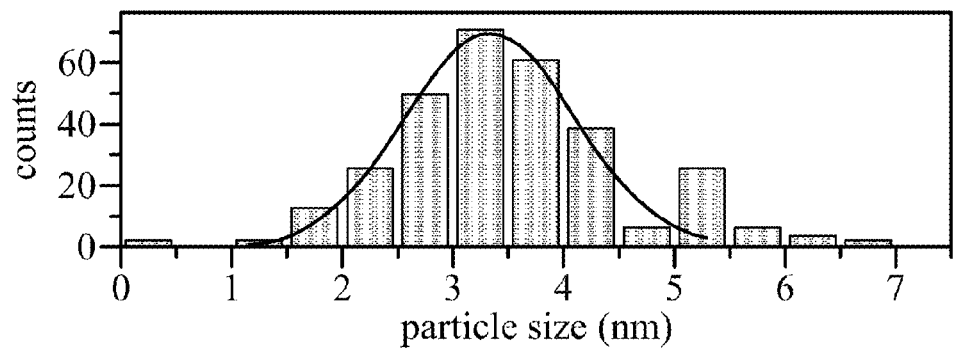
FIGS. 7A-7C are the distribution of the particle size of a nanodot in accordance with some embodiments of the present disclosure.
Figure 7B:
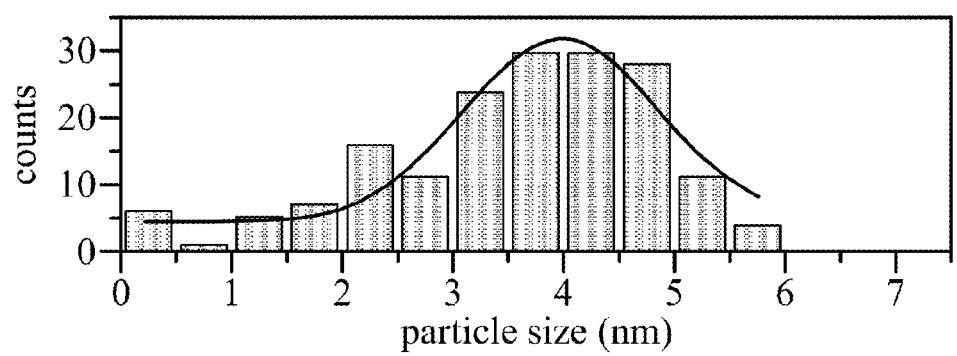
Figure 7C:
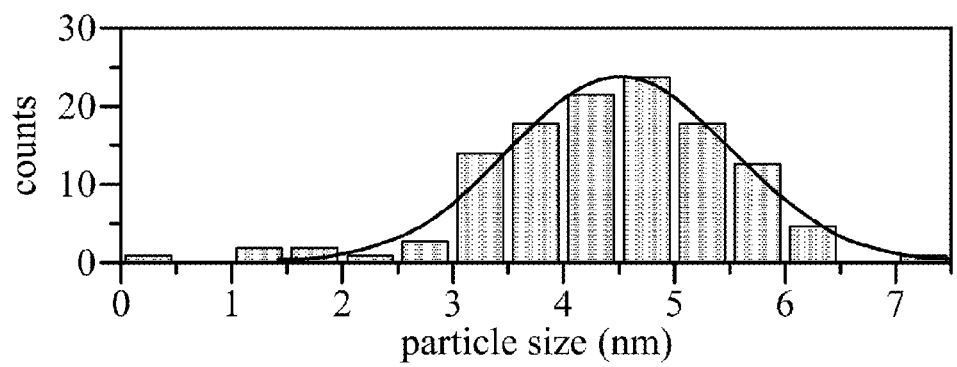

The nanodots prepared in examples 1-3 were analyzed by atomic force microscopy (AFM), as shown in FIGS. 6A-6C. These figures clearly indicate that the nanodot had a silicon oxide core and a self-assembled monolayer. FIG. 6A is the atomic force microscopy of n-hexyltriethoxysilane nanodot. FIG. 6B is the atomic force microscopy of n-docecyltriethoxysilane nanodot. FIG. 6C is the atomic force microscopy of an n-octadecyltriethoxysilane nanodot. The particle size distributions of n-hexyltriethoxysilane nanodot, n-docecyltriethoxysilane nanodot and n-octadecyltriethoxysi lane nanodot were calculated respectively from FIGS. 6A-6C, as shown in FIGS. 7A-7C. FIG. 7A shows that the particle size of n-hexyltriethoxysilane nanodot ranged from about 1.5 nm to 4.5 nm. FIG. 7B shows that the particle size of n-docecyltriethoxysilane nanodot ranged from about 2.5 nm to 5.5 nm. FIG. 7C shows that the particle size of an n-octadecyltriethoxysilane nanodot ranged from about 3 nm to 6.5 nm. Therefore, the particle size of the prepared nanodot could be controlled by choosing substituted or non-substituted hydrocarbon groups with different lengths.

[Optical Property Analysis]

Figure 8A:
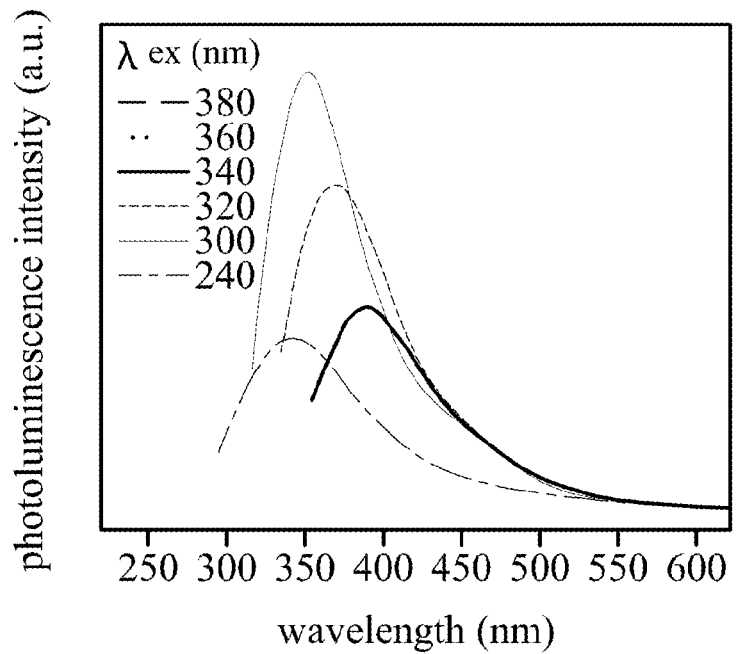
FIGS. 8A-8C are photoluminescence spectra of a nanodot in accordance with some embodiments of the present disclosure.
Figure 8B:
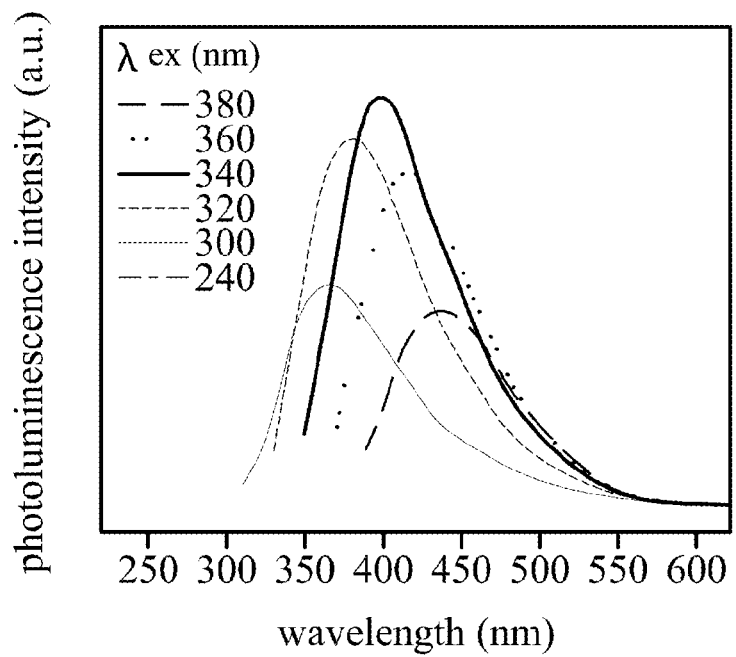
Figure 8C:
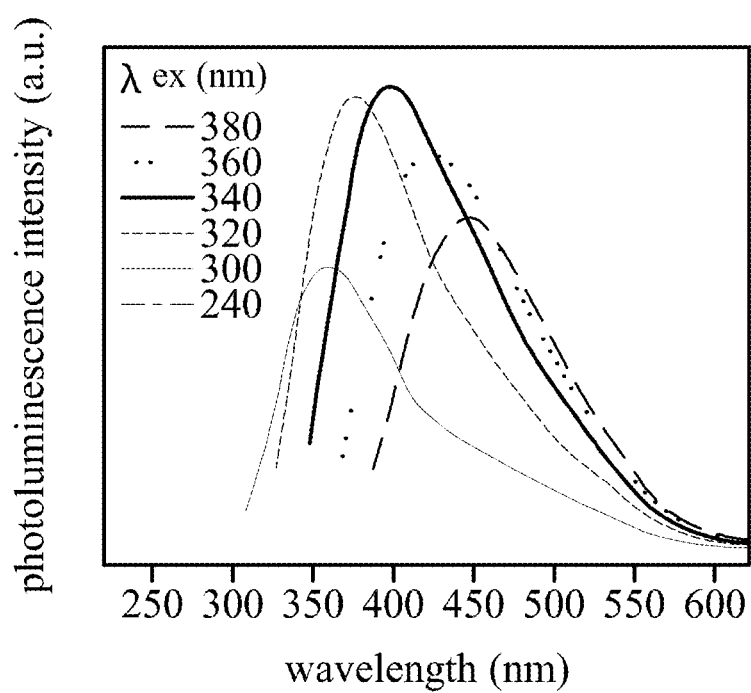
Figure 11B:
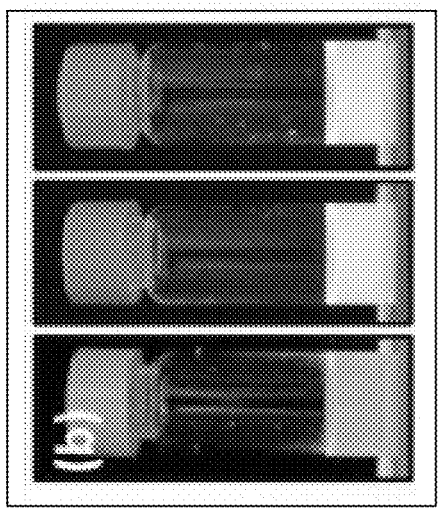
FIG. 11B is an image of nanodots under UV light.
Figure 11A:
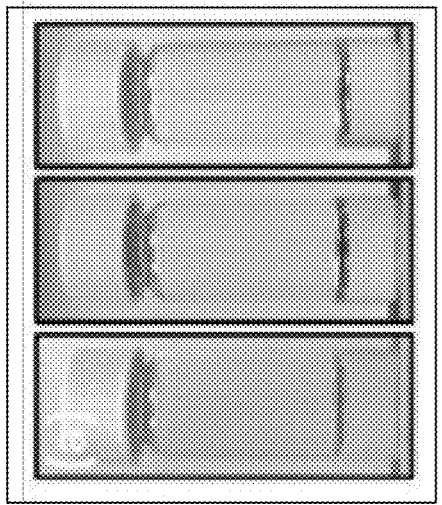
FIG. 11A is an image of nanodots under visible light.

The optical properties of the nanodots prepared in examples 1-3 were analyzed. FIGS. 8A-8C are photoluminescence spectroscopes of the nanodots prepared in examples 1-3. FIG. 8A shows that the n-hexyltriethoxysilane nanodot has an emission wavelength ranging from about 350 nm to 470 nm. FIG. 8B shows that the n-docecyltriethoxysilane nanodot has an emission wavelength ranging from about 340 nm to 530 nm. FIG. 8C shows that the n-octadecyltriethoxysilane nanodot has an emission wavelength ranging from about 330 nm to 570 nm. In addition, FIG. 11A is the images of the nanodots prepared in examples 1-3 under visible light (corresponding to examples 1-3 from left to right, respectively). FIG. 11B is the images of the nanodots prepared in examples 1-3 under UV light of 365 nm (corresponding to examples 1-3 from left to right, respectively). FIG. 11B indicates that the nanodot has a blue/white light emission property under UV light. In addition, by using the quantum yield test experiments discussed by Zhou et al. (An electrochemical avenue to blue luminescent nanocrystals from multiwalled carbon nanotubes (MWCNTs). J. Am. Chem. Soc. 129, 744-745(2007)), the quantum yield of n-hexyltriethoxysilane nanodot could be determined and was 3.1%. The quantum yield of n-docecyltriethoxysilane nanodot could be determined and was 28.8%. The quantum yield of an n-octadecyltriethoxysilane nanodot could be determined and was 45.6%. Therefore, the nanodot of the present disclosure has good multiphoton fluorescence property.

[In vivo Cytotoxicity Measurement]

Figure 9:
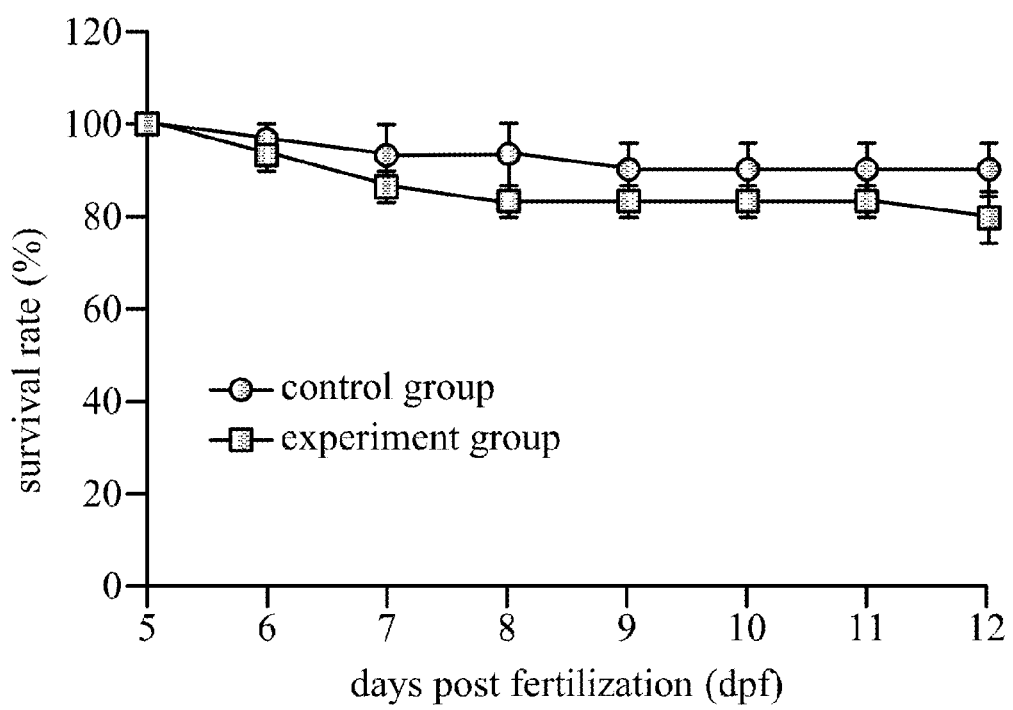
FIG. 9 is a survival rate analytical diagram of an in vivo toxicity test of a nanodot in accordance with some embodiments of the present disclosure.

The in vim cytotoxicity measurement of an n-octadecyltriethoxysilane nanodot was performed with zebrafish as a target. The n-octadecyltriethoxysilane nanodot and feed were mixed and the five-day-old zebrafish was fed with the mixture. The nanodot/feed mixture was prepared at a weight ratio of 1:1. The fed zebrafish was monitored until 12 days post fertilization (dpf). Referring to FIG. 9, the survival rate of the control group was 90±10%, while the survival rate of the zebrafish fed with the nanodot (experiment group) was 80±10%. Therefore, it was shown that the nanodot had good biocompatibility.

[Intravital Imaging]

Figure 12:
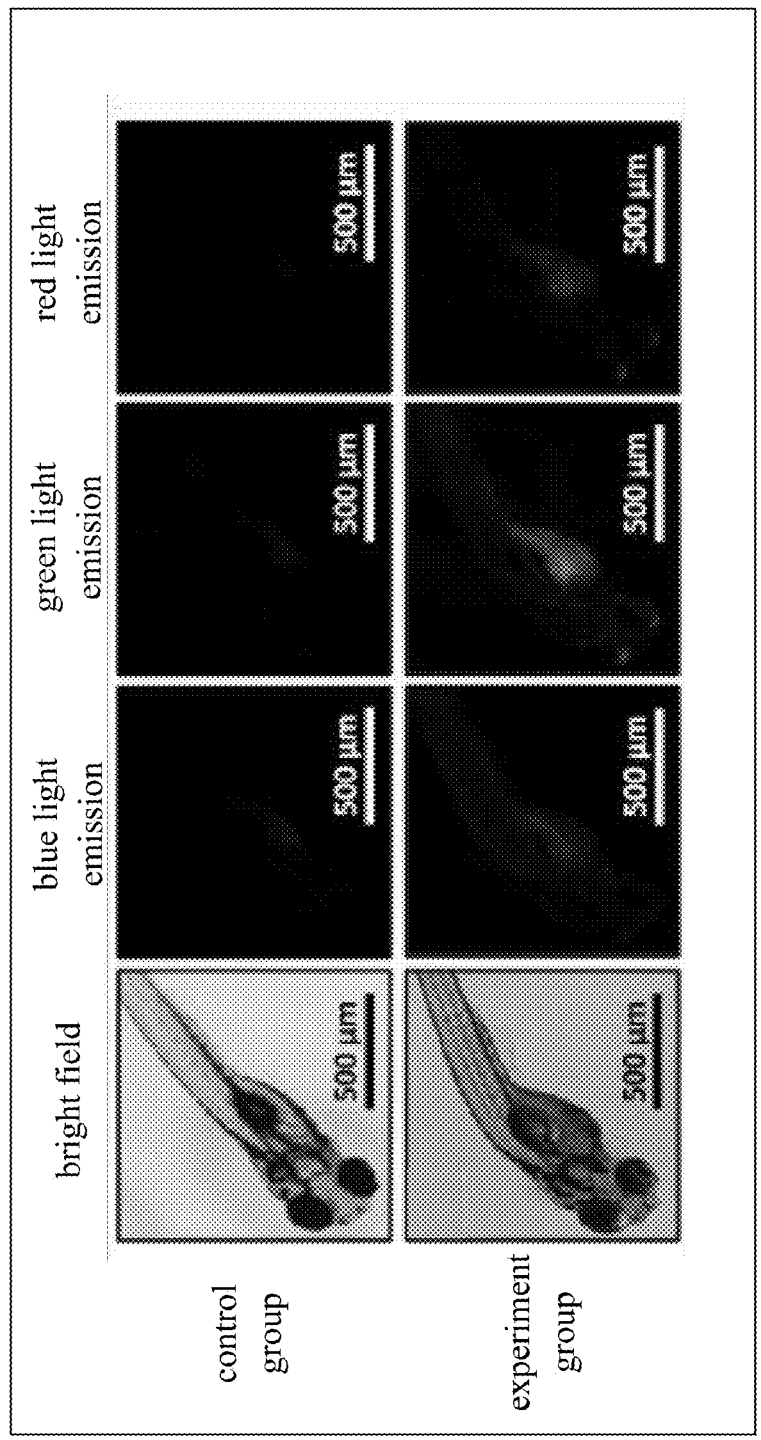
FIG. 12 is a fluorescence microscopy of a control group and an experiment group under a bright field or under other different excitation light sources.

The intravital imaging was performed by using n-octadecyltriethoxysilane nanodot with zebrafish as a target. The n-octadecyltriethoxysilane nanodot and feed were mixed and the five-day-old zebrafish was fed with the mixture. The nanodot/feed mixture was prepared at a weight ratio of 1:1. After 90 minutes from feeding, the fed zebrafish was observed by fluorescence microscope. As shown in FIG. 12, the upper row was the control group, while the lower row was the experiment group. This figure shows that the nanodot exhibited significant multiphoton fluorescence with red, green and blue lights emitted when excited by an excitation light with different wavelengths.

Example 4

3-Aminopropyltriethoxysilane (purity>99%) was purchased from Sigma-Aldrich (USA) and used without further purification. 3-Aminopropyltriethoxysilane was heated at to 200° C. and stirred (1100 rpm) at a constant temperature of 200° C. for 4 hours to prepare 3-aminopropyltriethoxysilane nanodot solution. The self-assembled monolayer of this 3-aminopropyltriethoxysilane nanodot had a terminal amino group.

[Avidin Modification]

1 mL 3-aminopropyltriethoxysilane nanodot solution prepared in example 4 was added into 7 mL Dutbecco's Modified Eagle's Medium (DMEM) to form a mixed solution. The pH value of this mixed solution was altered to 7.0-7.3 by adding acetic acid. Then 1.0 mg avidin (purchased from Sigma) was added into 1 µL mixed solution and was uniformly mixed. After 15 minutes at room temperature, an avidin modified 3-aminopropyltriethoxysilane nanodot was prepared. Then the pH value of this solution was altered to 7.0-7.3 by adding acetic acid. 0.2 µm sterile filter (purchased from Minipore) was used to separate the avidin modified 3-aminopropyltriethoxysilane nanodot.

[Galactose Modification]

1 mL 3-aminopropyltriethoxysilane nanodot solution prepared in example 4 was added into 7 mL Dutbecco's Modified Eagle's Medium (DMEM) to form a mixed solution. The pH value of this mixed solution was altered to 7.0-7.3 by adding acetic acid. Then 1.0 mg galactose (purchased from Sigma) was added into 1 µL mixed solution and was uniformly mixed. After 15 minutes at room temperature, a galactose modified 3-aminopropyltriethoxysilane nanodot was prepared. Then the pH value of this solution was altered to 7.0-7.3 by adding acetic acid. 0.2 µm sterile filter (purchased from Minipore) was used to separate the galactose modified 3-aminopropyltriethoxysilane nanodot.

[Bioprobing and Bioimaging]

Figure 13:
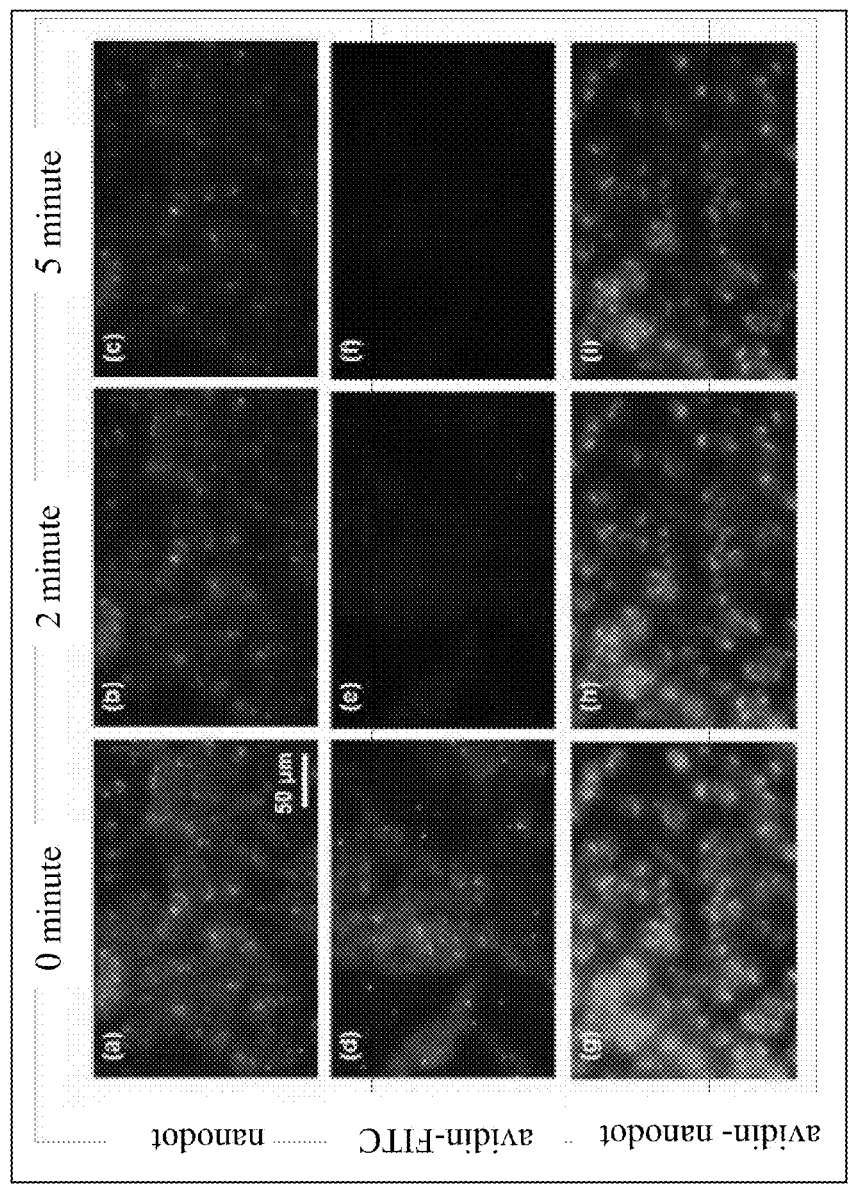
FIG. 13 is a fluorescence microscopy with nanodot, avidin-FITC or avidin-nanodot at different time.

SK-Hep-1 cell was incubated under 37° C. for 12 hours (overnight). Then the 3-aminopropyltriethoxysilane nanodot solution (20 mM) prepared in example 4 and the avidin modified 3-aminopropyltriethoxysilane nanodot solution (20 mM) were added into this SK-Hep-1 cell to form two cell cultures respectively. After 48 hours, the cell culture was rinsed with PBS (phosphate buffered saline). Then the cell was fixed by paraformaldehyde. The cell culture was perfused by 2% Triton X-100 (also referred to as polyethylene glycol p-(1,1,3, 3-tetramethylbutyl)-phenyl ether) and was observed by an inverted fluorescence microscope (Leica, DMIL, Germany). Referring to FIG. 10, FIGS. 10(a)-(d) show the SK-Hep-1 cell added with 3-aminopropyltriethoxysilane nanodot solution. FIGS. 10(m)-(p) show the SK-Hep-1 cell added with avidin modified 3-aminopropyltriethoxysilane nanodot solution. This figure shows that the nanodot exhibited significant multiphoton fluorescence with red, green and blue lights emitted when excited by an excitation light with different wavelengths. Comparing FIGS. 10(b)-(d) with FIGS. 10(n)-(p), avidin modification could enhance the efficiency of the nanodot to enter into cells and aggregate in cells. FIGS. 10(e)-(h) show the SK-Hep-1 cell added with avidin only, which showed no fluorescence signal. Therefore, the fluorescence signal of FIGS. 10(b)-(d) and (n)-(p) resulted from the nanodot. In addition, FIGS. 10(i)-(I) show the SK-Hep-1 cell added with avidin-FITC. This figure shows that FITC could not emit blue and red fluorescence. Furthermore, stability measurements of the nanodot and FITC were performed, as shown in FIG. 13. FIGS. 13(a)-(c) show the images of the SK-Hep-1 cell added with 3-aminopropyltriethoxysilane nanodot solution and continuously irradiated with excitation light, wherein FIGS. 13(a)-(c) are the images observed at 0 minutes, 2 minutes and 5 minutes respectively. FIGS. 13(d)-(f) show the images of the SK-Hep-1 cell added with avidin- FITC and continuously irradiated with excitation light, wherein FIGS. 13(d)-(f) are the images observed at 0 minutes, 2 minutes and 5 minutes respectively. FIGS. 13(g)-(i) show the images of the SK-Hep-1 cell added with avidin modified 3-aminopropyltriethoxysilane nanodot solution and continuously irradiated with excitation light, wherein FIGS. 13(g)-(i) are the images observed at 0 minutes, 2 minutes and 5 minutes respectively. As shown in these figures, FITC exhibited nearly no fluorescence at 2 minutes and 5 minutes. In comparison, the fluorescence exhibited by the nanodot only became slightly weak. Therefore, the nanodot has better photo stability.

[Bioprobing and Bioimaging]

Figure 14:
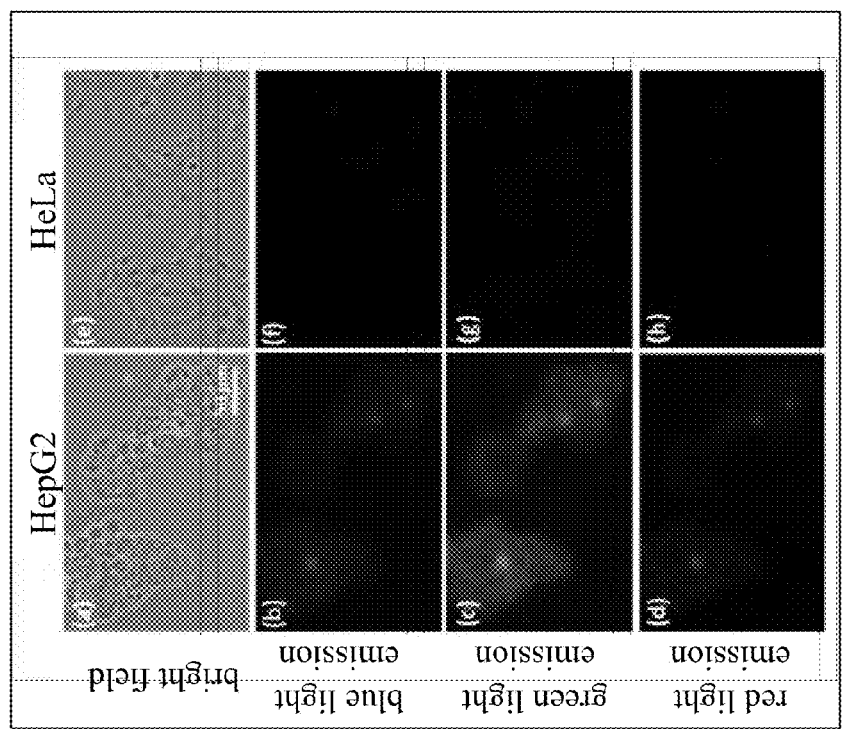
FIG. 14 is a fluorescence microscopy of HepG2 cell and HeLa cell.

HepG2 cell and HeLa cell were incubated under 37° C. for 12 hours (overnight). Then the galactose modified 3-aminopropyltriethoxysilane nanodot was added into this HepG2 cell and HeLa cell to form a cell culture, respectively. After 2 hours, the cell culture was rinsed with PBS (phosphate buffered saline). Then the cell was fixed by paraformaldehyde. The cell culture was perfused by 2% Triton X-100 (also referred to as polyethylene glycol p-(1,1,3,3-tetramethylbutyl)-phenyl ether) and was observed by an inverted fluorescence microscope (Leica, DMIL, Germany). Referring to FIG. 14, FIGS. 14(a)-(d) show the images of the HepG2 cell added with galactose modified 3-aminopropyltriethoxysilane nanodot under a bright field or under other different excitation light sources. FIGS. 14(e)-(h) show the images of the HeLa cell added with galactose modified 3-aminopropyltriethoxysilane nanodot under a bright field or under other different excitation light sources. Since HepG2 cell could express asialoglycoprotein receptor (ASGPR) at its cell surface, the galactose modified at the nanodot could specifically interact with the asialoglycoprotein receptor and enter the HepG2 cell. In comparison, since HeLa cell did not have asialoglycoprotein receptor, the nanodot could not enter the HeLa cell. Therefore, FIGS. 14(f)-(h) show no fluorescence signal. In summary, by being modified with a specific group, the nanodot could detect a specific biomolecule. Therefore, modified nanodots can be applied in biotargeting, bioprobing and biosensing.

Although some embodiments of the present disclosure and their advantages have been described in detail, it should be understood that various changes, substitutions and alterations can be made herein without departing from the spirit and scope of the disclosure as defined by the appended claims. For example, it will be readily understood by those skilled in the art that many of the features, functions, processes, and materials described herein may be varied while remaining within the scope of the present disclosure. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for manufacturing a nanodot, comprising:
providing a hydrolysable silane, wherein the hydrolysable silane has one or more hydrolysable groups and one or more substituted or non-substituted hydrocarbon groups; and
performing a one-step heat treatment to hydrolyze and condensate the hydrolysable silane to form a nanodot, wherein the nanodot comprises:
a core, the core is selected from the group consisting of a semiconductor core or a metal core, wherein the core consists of a silicon oxide core; and
a self-assembled monolayer (SAM) comprising the substituted or non-substituted hydrocarbon groups, wherein the self-assembled monolayer is connected to the core by covalent bonds.

2. The method as claimed in claim 1, wherein the substituted or non-substituted hydrocarbon groups comprise 2-33 carbon atoms.

3. The method as claimed in claim 1, wherein the one-step heat treatment is performed at a temperature ranging from 120° C. to 220° C. for 30 minutes to 9 hours.

4. The method as claimed in claim 1, wherein the hydrolysable groups comprises a halogen or alkoxy group.

5. The method as claimed in claim 1, wherein the substituent group of the hydrocarbon groups comprises an alkyl group, a haloalkyl group, a thiol group, an amino group or an aryl group.

6. The method as claimed in claim 1, wherein the hydrolysable silane has a general formula of $SiR^1_x R^2_{(4-x)}$, wherein
x is 2 or 3,
$R^1$ is a halogen or $C_1$ to $C_5$ alkoxy group, and
$R^2$ is the substituted or non-substituted hydrocarbon groups and the substituent group is an alkyl group, a haloalkyl group, a thiol group, an amino group or an aryl group.

7. The method as claimed in claim 1, wherein the hydrocarbon groups have a terminal amino group.

8. The method as claimed in claim 1, after the one-step heat treatment, further comprising adding a protein molecule or a saccharide molecule to modify the self-assembled monolayer.

9. The method as claimed in claim 1, wherein the nanodot has an emission wavelength ranging from 300 nm to 600 nm.

* * * * *